United States Patent [19]

Smith et al.

[11] Patent Number: 4,467,046

[45] Date of Patent: Aug. 21, 1984

[54] DEHYDROGENATION CATALYST

[76] Inventors: James L. Smith, 8805 High Point Cir., Louisville, Ky. 40299; Bill S. Masters, 8000 Troutwood Ct., Louisville, Ky. 40291; Dennis J. Smith, 10708 Blackwood Rd., Jeffersontown, Ky. 40299

[21] Appl. No.: 337,943

[22] Filed: Jan. 7, 1982

[51] Int. Cl.$^3$ .................. B01J 23/10; B01J 23/78; B01J 23/88; B01J 27/20
[52] U.S. Cl. ................................ 502/174; 502/304; 585/445
[58] Field of Search ............... 252/443, 462; 585/445; 502/174, 304

[56] References Cited

U.S. PATENT DOCUMENTS 3,904,552  9/1975  O'Hara ........................ 252/462 X
4,144,197  3/1979  Riesser ........................... 252/462

FOREIGN PATENT DOCUMENTS 162134  4/1964  U.S.S.R. ........................ 585/445

Primary Examiner—W. J. Shine

[57] ABSTRACT

Catalysts found to be particularly effective in the dehydrogenation of alkyl aromatics, for example ethylbenzene to styrene, where the catalysts include iron oxide, 12 to 30% of an alkali metal compound, 3 to 7% of a cerium compound, 1.5 to 6.0% of a molybdenum compound and 1 to 8% of a calcium compound. Catalyst can also include 0 to 8.0% of a chromium compound.

5 Claims, 4 Drawing Figures

DEHYDROGENATION CATALYST

BACKGROUND OF THE INVENTION

This invention relates generally to a catalyst and method for production of olefins by dehydrogenation of alkyl aromatics and more specifically to the composition and use of an improved dehydrogenation catalyst.

The prior art dehydrogenation catalysts used in the dehydrogenation of alkyl aromatics to alkene aromatics, for example, ethylbenzene to styrene as previously discussed, and alkanyl pyridines to alkenyl pyridines are widely known. Various catalysts, the dehydrogenation conditions and other operating data are disclosed in Pitzer, U.S. Pat. No. 2,866,790 relating to the use of a catalyst composition including potassium carbonate, chromium oxide and iron oxide. Other catalysts and procedures are also shown in Gutzeith, U.S. Pat. No. 2,408,140; Eggersten, et al, U.S. Pat. No. 2,414,585; Hills, et al, U.S. Pat. No. 3,360,579; U.S. Pat. No. 3,364,277; and U.S. Pat. No. 4,098,723.

U.S. Pat. No. 4,144,197 discloses the use of a catalyst composition including ferric oxides, potassium oxide, vanadium oxide, molybdenum oxide, chromium oxide cerium oxide, and cobalt oxide.

U.S. Pat. No. 3,904,552-O'Hara discloses the use of a catalyst containing ferric oxide, alkali metal salts, molybdenum oxide and cerium oxide.

While certain prior art references such as U.S. Pat. Nos. 3,904,552 and 2,990,432 teach use of Portland cement for promotion of structural stability, where the Portland cement includes calcium, it has been unexpectedly found that use of calcium provides a synergistic effect which enhances the catalyst performance, and particularly performance stability beyond that achieved by use of Portland Cement. It is believed that the inclusion of a calcium compound provides stabilization of the molybdenum component during high temperature calcination.

Additionally, catalysts within the scope of the present invention provide high selectivity by inclusion of cerium and molybdenum promoters which are further enhanced by the composition of the present invention.

Facilities for dehydrogenation of organic materials, particularly for the dehydrogenation of alkyl aromatics to alkenyl aromatics, are normally operated at the highest practical throughout rates to obtain optimum yield. Yield is dependent on conversion and selectivity of the catalyst.

Selectivity of the catalyst is defined as the proportion of the desired product (for example, styrene) produced to the total amount of feedstock (for example, ethylbenzene) converted. Activity or conversion is the representation of that portion of the feedstock converted both to the desired product and to by-products.

It is recognized that improvements in either selectivity or activity but particularly selectivity of a dehydrogenation catalyst can result in substantially improved operating efficiency.

It is generally very difficult to obtain a catalyst which has both high selectivity and high activity because high selectivity is generally accompanied by low conversion and vice versa. In general, higher conversion in catalytic dehydrogenation is favored by higher temperatures. However, higher temperatures generally result in increased production of by products and thus low selectivity. In the conversion of ethylbenzene to styrene, the predominant by-products are benzene and toluene. The benzene produced can be recycled for later processing but toluene cannot be easily recycled and is considered an undesirable by-product so that the ratio of benzene to toluene in the final product is another criteria of the effectiveness of the catalyst in this application.

It is well known that the activity of some dehydrogenation catalysts diminish with time. Ultimately, the activity of the catalyst is reduced to the point where the catalyst must be regenerated. The regeneration is accomplished by taking the production unit off stream and regenerating the catalyst by steaming. Regeneration is costly because of lost production time and due to the cost of the energy necessary to produce steam.

Accordingly, any increased stability of the catalyst, that is, long term use without diminished activity requiring regeneration enhances the economics of any process using a catalyst.

SUMMARY OF THE INVENTION

The present invention provides a new and useful catalyst for the production of olefinic compounds by dehydrogenation of more saturated materials, where the catalyst unexpectedly maintains high activity and selectivity over an extended period of time, and further has enhanced selectivity at high conversion.

The present invention further provides a catalyst which demonstrates improved performance stability over a wide range of operating conditions and further demonstrates satisfactory and, in some cases, improved conversion and selectivity in the dehydrogenation of ethylbenzene to styrene.

Because of the improved stability of catalysts in accordance with the present invention, longer operating time is permitted between regeneration with a consequent savings in energy costs and improved overall operating efficiency through longer "on stream time" between regeneration periods.

More particularly, the present invention provides catalysts found to be effective in the dehydrogenation of alkyl aromatics, and particularly ethylbenzene, to olefinic compounds where the catalysts include 15 to 30% of an alkali metal compound, for example potassium oxide; 2.0 to 8.0% of a chromium compound, for example chromium oxide; 3 to 7% cerium compound, for example cerium oxide; 1.5 to 6.0% molybdenum compound, for example molybdenum oxide; and 1 to 8% calcium compound, for example calcium carbonate or hydroxide; and the balance iron oxide.

Various compositions within the scope of the present invention will occur to those skilled in the art upon reading of the disclosure set forth hereinafter.

BRIEF DESCRIPTION OF THE DRAWINGS

Operating characteristics of one example of a catalyst within the scope of the present invention as compared with other prior art catalysts are shown in the accompanying drawings wherein.

Figure 1:
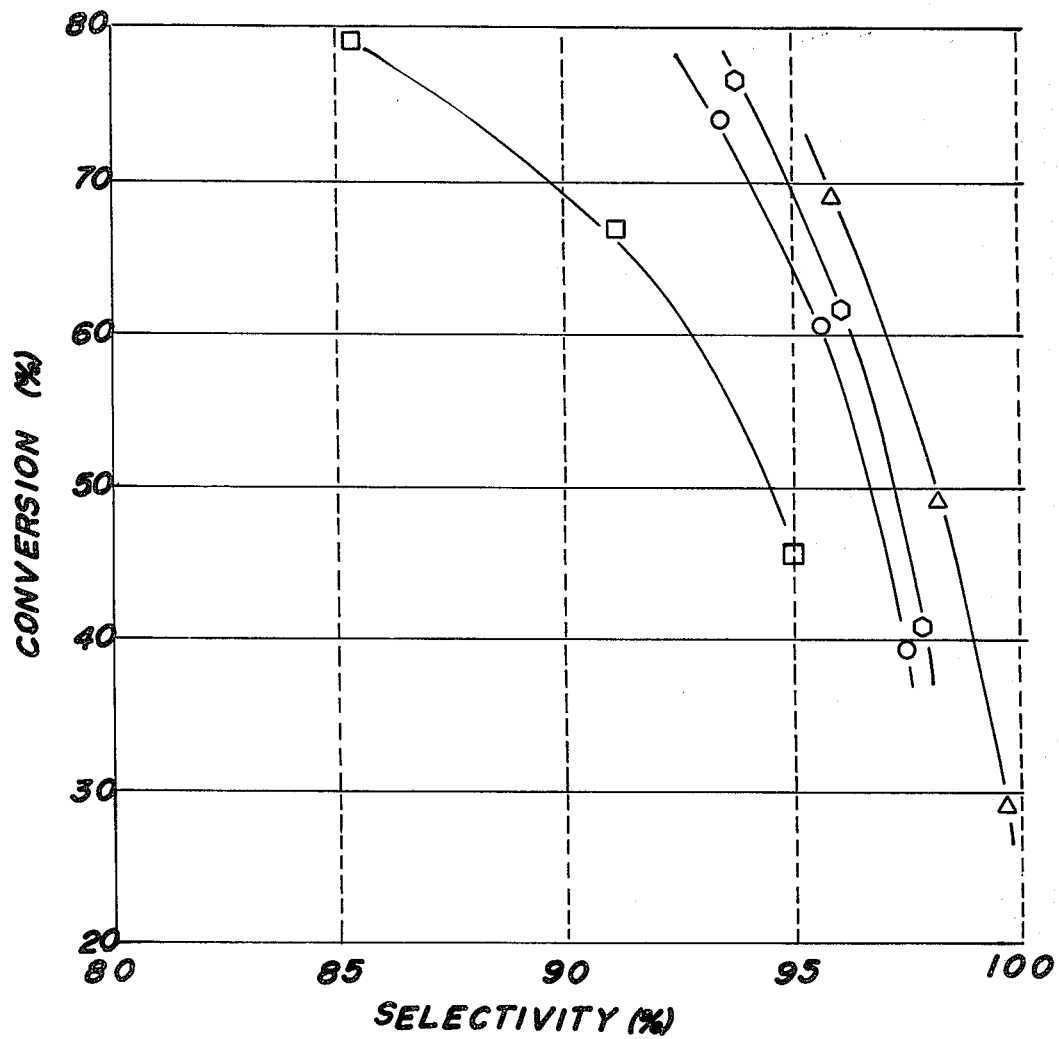
FIG. 1 is a chart of examples of selectivity and conversion for various comparison catalysts as well as a catalyst of the present invention.

Satisfactory catalysts within the scope of the present invention have been prepared having compositions of:
- 15% to 30% $K_2O$
- 2% to 8% $CeO_2$
- 1.5% to 6% $MoO_3$
- 1% to 4% $CaCO_3$
- Balance $Fe_2O_3$ Also, the catalyst can include 0 to 8% chromium compound, for example $Cr_2O_3$, which has been found, within the scope of the present invention to increase the active life of the catalyst.

While the foregoing compound are utilized in the example of the present invention as described hereinafter, it will be recognized that other salts of the designated metals are satisfactory for use in the catalyst.

Three blends were prepared within the aforenoted ranges where the Ce, Mo, Ca, Fe and Cr components are blended. The mixture is then dry mixed and the potassium added as the hydroxide during a subsequent mixing steps to form a paste. The paste is then extruded to form pellets. The pellets are then dried and calcined.

The three blends compounded yielded catalysts with the following compositions:

EXAMPLE I

| | |
|---|---|
| 70.6% | $Fe_2O_3$ |
| 17.0% | $K_2O$ |
| 6.6% | $CeO_2$ |
| 1.7% | $Cr_2O_3$ |
| 2.5% | $MoO_3$ |
| 2.8% | $CaCO_3$ |

EXAMPLE II

| | |
|---|---|
| 74.4 | $Fe_2O_3$ |
| 15.3 | $K_2O$ |
| 5.2 | $CeO_2$ |
| 1.9 | $Cr_2O_3$ |
| 1.8 | $MoO_3$ |
| 1.4 | $CaCo_3$ |

EXAMPLE III

| | |
|---|---|
| 73.9 | $Fe_2O_3$ |
| 16.0 | $K_2O$ |
| 5.2 | $CeO_2$ |
| 1.8 | $Cr_2O_3$ |
| 1.9 | $MoO_3$ |
| 1.6 | $CaCO_3$ |

The catalysts of the examples I–III are generally equally satisfactory in dehydrogenation operation.

A catalyst in accordance with the present invention as previously described in Example I was compared in the dehydrogenation of ethylbenzene with Comparison Catalysts I-III having the following compositions:

COMPARISON CATALYST I

| COMPONENT | WEIGHT PERCENT |
|---|---|
| $Fe_2O_3$ | 75.0% |
| $K_2CO_3$ | 23.0% |
| $Cr_2O_3$ | 2.0% |

COMPARISON CATALYST II

| COMPONENT | WEIGHT PERCENT |
|---|---|
| $Fe_2O_3$ | 58.0 |
| $K_2CO_3$ | 23.0 |
| $Ce_2O_3$ | 5.5 |
| $MoO_3$ | 2.5 |
| Cement | 11.0 |

COMPARISON CATALYST III

| COMPONENT | WEIGHT PERCENT |
|---|---|
| $Fe_2O_3$ | 52.2 |
| $K_2CO_3$ | 33.0 |
| $MoO_3$ | 2.5 |
| $CeO_2$ | 5.3 |
| Cement | 7.0 |

Each of the Comparison Catalysts and the invention catalyst were tested over a selected period of time at constant test conditions: namely LHSV (Liquid Hourly Space Velocity) of 1.0, a steam to oil weight ratio of 2.0, at atmospheric pressure utilizing 100 cc of each of the catalysts. The feed in each case was 99%+ purity ethylbenzene. All of the tests were made using the same test equipment.

The testing provided the results set forth in Table I, where catalyst performance is indicated in terms of conversion, yield, and selectivity.

TABLE I

| Catalyst | OPR. HRS | TEMP °F. | % Conv. | % Yield | % Select. |
|---|---|---|---|---|---|
| Invention Catalyst Example I | 268.0 | 1050 | 29.4 | 29.3 | 99.7 |
| | 288.0 | 1050 | 28.3 | 28.3 | 99.9 |
| | 316.0 | 1100 | 49.5 | 48.7 | 98.4 |
| | 337.0 | 1100 | 49.3 | 48.6 | 98.4 |
| | 362.0 | 1150 | 68.7 | 66.2 | 96.4 |
| | 382.5 | 1150 | 68.2 | 65.8 | 96.5 |
| Comparison Catalyst I | 21.5 | 1150 | 76.4 | 66.6 | 87.2 |
| | 67.5 | 1150 | 78.8 | 67.5 | 85.7 |
| | 88.5 | 1150 | 78.7 | 67.5 | 85.8 |
| | 112.5 | 1100 | 64.8 | 59.2 | 91.4 |
| | 138.5 | 1100 | 65.2 | 59.6 | 91.4 |
| | 162.5 | 1050 | 45.4 | 43.1 | 94.9 |
| | 186.0 | 1050 | 44.8 | 42.5 | 94.9 |
| Comparison Catalyst II | 214.5 | 1150 | 75.6 | 70.7 | 93.5 |
| | 236.5 | 1100 | 61.0 | 58.7 | 96.2 |
| | 262.0 | 1050 | 39.9 | 39.2 | 98.2 |
| | 286.0 | 1050 | 39.2 | 38.5 | 98.3 |
| Comparison Catalyst III | 26.0 | 1150 | 73.0 | 67.8 | 92.9 |
| | 45.5 | 1150 | 76.0 | 70.7 | 93.0 |
| | 70.0 | 1150 | 76.9 | 72.0 | 93.6 |
| | 94.0 | 1150 | 77.6 | 72.6 | 93.6 |
| | 120.5 | 1150 | 77.1 | 72.2 | 93.6 |
| | 145.5 | 1100 | 62.4 | 60.3 | 96.6 |
| | 167.5 | 1100 | 61.8 | 59.7 | 96.7 |
| | 192.5 | 1050 | 41.1 | 40.5 | 98.4 |
| | 213.5 | 1050 | 41.3 | 40.7 | 98.5 |

Constant Test Conditions: 1.0 LHSV, 2.0 S/O wt, 1 atm. 100 cc catalyst.
Feed: Ethylbenzene, 99+% purity.

The results of the test are graphically represented in FIG. 1 where a plot of conversion versus selectivity is utilized to compare the effectiveness of each of the catalysts.

As previously noted the comparison of conversion and selectivity is a recognized means of comparing overall efficiency of a catalyst inasmuch as it is an indication of the proportion of the desired product produced by the catalyst at different rates of conversion.

Considering FIG. 1, it will be noted that the invention catalyst is superior in terms of selectivity to all other catalysts by a marked degree and demonstrates the unexpected advantages provided by the invention catalyst.

It will be further noted that comparison catalysts II and III include cement and the data illustrate the superiority of catalyst utilizing $CaCO_3$ without the Portland cement.

In an effort to gain additional insight into the long term stability of the invention catalyst, a life test of approximately 1000 hours was undertaken on the catalyst of Example I as well as comparison catalyst I—a commercial catalyst known to exhibit stable performance. This testing was conducted at contant test conditions of 1.0 LHSV, 2.0 S/O, 4 psig, and 1150° F.

Figure 2:
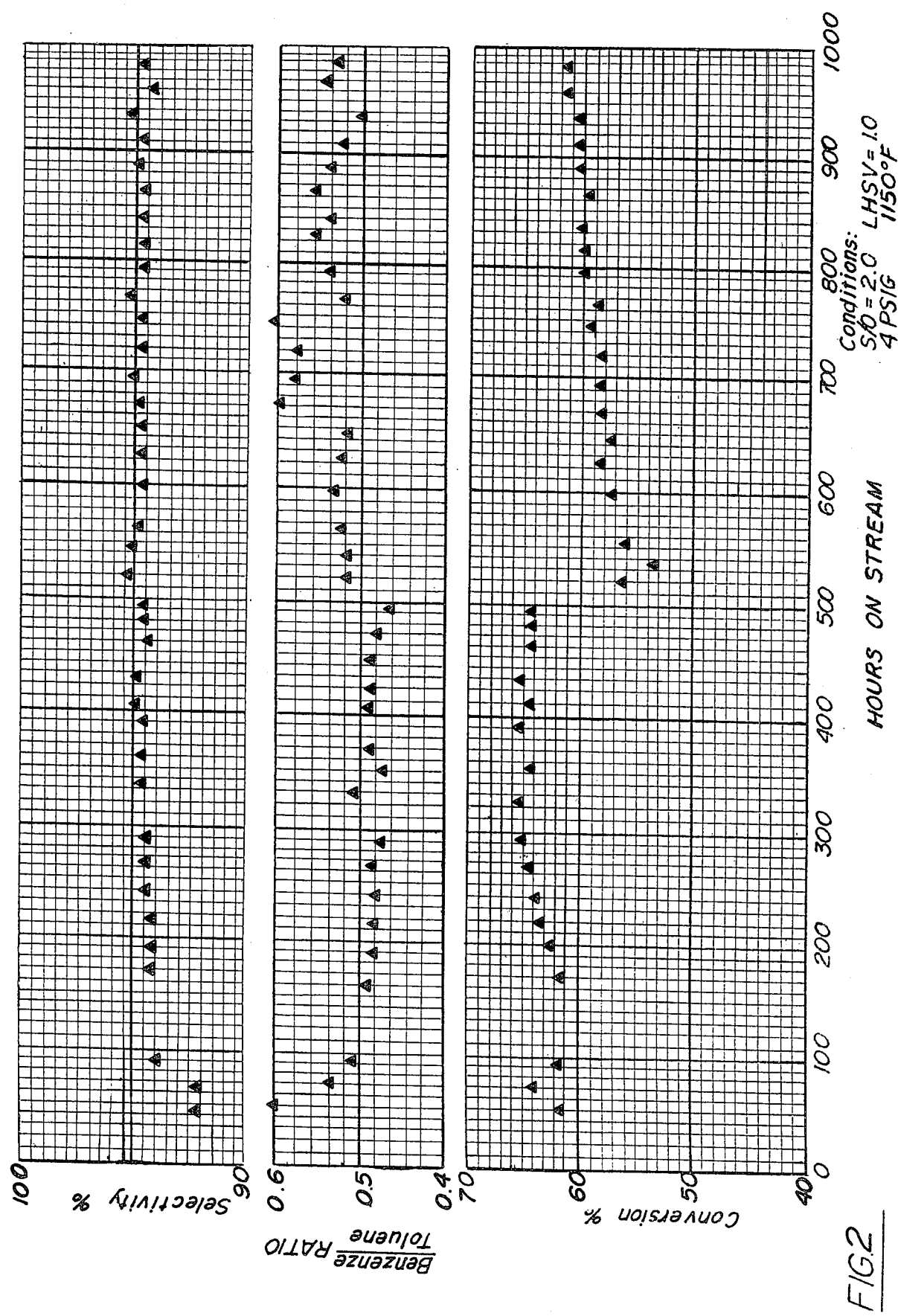
FIG. 2 is a graphic representation of performance characteristics of the invention catalyst over an approximately 1000 hour test period.
Figure 3:
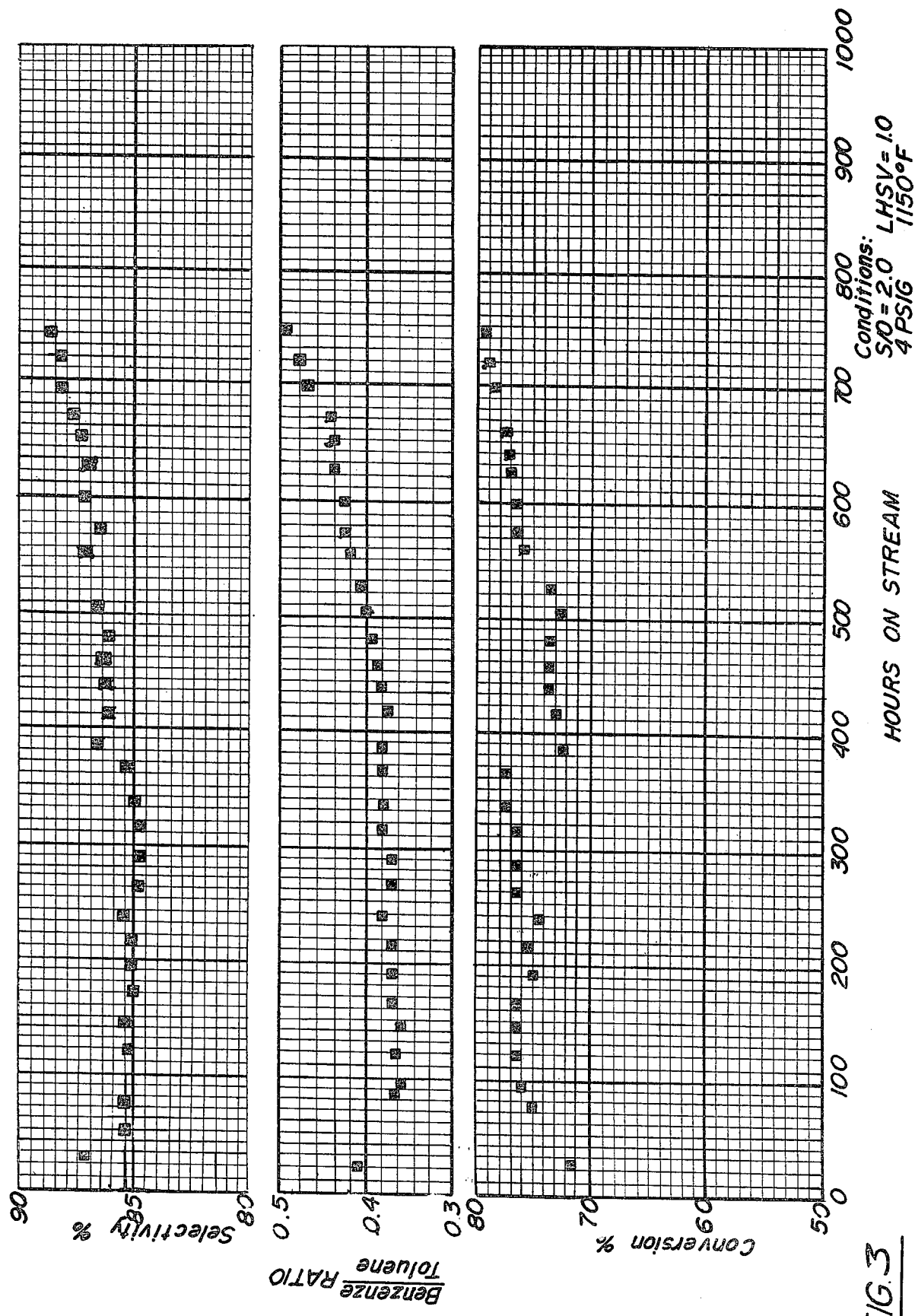
FIG. 3 is a similar representation to FIG. 2 showing the performance characteristics of Comparison Catalyst I.

Results of this testing are reported in Tables II and III and FIGS. 2 and 3. These data are not intended for direct comparison insofar as catalyst performance is concerned since they were obtained in different test units, but are presented to show the comparative degree of stability of each catalyst. This data shows that the invention catalyst is no less stable than comparison catalyst I.

TABLE II

| Catalyst | OPR. HRS | TEMP °F. | % Conv | % Yield | % Select | B/T |
|---|---|---|---|---|---|---|
| Invention | 51.5 | 1150 | 61.9 | 57.1 | 92.2 | 0.62 |
| Catalyst | 72.0 | 1150 | 64.1 | 59.2 | 92.4 | 0.54 |
| Example I | 96.0 | 1150 | 61.7 | 57.9 | 93.8 | 0.51 |
| | 168.5 | 1150 | 61.5 | 58.1 | 94.5 | 0.49 |
| | 190.5 | 1150 | 62.7 | 59.3 | 94.6 | 0.48 |
| | 215.0 | 1150 | 63.0 | 59.5 | 94.4 | 0.46 |
| | 240.5 | 1150 | 63.6 | 60.1 | 94.5 | 0.46 |
| | 264.0 | 1150 | 64.6 | 61.0 | 94.4 | 0.48 |
| | 288.0 | 1150 | 65.0 | 61.4 | 94.5 | 0.47 |
| | 336.0 | 1150 | 65.7 | 62.2 | 94.6 | 0.50 |
| | 362.0 | 1150 | 64.7 | 61.2 | 94.4 | 0.47 |
| | 387.5 | 1150 | 66.6 | 62.9 | 94.6 | 0.49 |
| | 407.5 | 1150 | 64.9 | 61.4 | 94.5 | 0.49 |
| | 429.0 | 1150 | 66.0 | 62.4 | 94.5 | 0.49 |
| | 456.5 | 1150 | 64.6 | 60.9 | 94.3 | 0.49 |
| | 480.0 | 1150 | 64.2 | 60.7 | 94.5 | 0.48 |
| | 503.5 | 1150 | 64.1 | 60.6 | 94.5 | 0.46 |
| | 527.5 | Temporarily lost ethylbenzene feed. | | | | |
| | 531.5 | 1150 | 56.9 | 54.4 | 95.6 | 0.52 |
| | 553.5 | 1150 | 54.0 | 51.3 | 95.0 | 0.52 |
| | 576.0 | 1150 | 56.9 | 53.9 | 94.7 | 0.55 |
| | 599.5 | 1150 | 57.8 | 54.7 | 94.6 | 0.56 |
| | 623.5 | 1150 | 58.5 | 55.3 | 94.7 | 0.53 |
| | 628.0 | 1150 | 58.5 | 55.4 | 94.7 | 0.53 |
| | 646.5 | 1150 | 57.5 | 54.5 | 94.7 | 0.52 |
| | 671.5 | 1150 | 58.8 | 55.8 | 94.9 | 0.60 |
| | 695.0 | 1150 | 58.4 | 55.5 | 95.0 | 0.58 |
| | 719.5 | 1150 | 58.6 | 55.6 | 94.8 | 0.58 |
| | 743.0 | 1150 | 60.0 | 56.8 | 94.7 | 0.61 |
| | 767.0 | 1150 | 59.6 | 56.7 | 95.1 | 0.52 |
| | 792.0 | 1150 | 60.4 | 57.2 | 94.6 | 0.54 |
| | 816.0 | 1150 | 60.5 | 57.2 | 94.6 | 0.56 |
| | 839.0 | 1150 | 60.3 | 57.1 | 94.7 | 0.54 |
| | 865.0 | 1150 | 59.8 | 56.7 | 94.7 | 0.56 |
| | 887.5 | 1150 | 60.8 | 57.8 | 95.1 | 0.54 |
| | 910.5 | 1150 | 60.6 | 57.4 | 94.8 | 0.53 |
| | 936.5 | 1150 | 60.7 | 57.9 | 95.3 | 0.50 |
| | 959.0 | 1150 | 61.5 | 58.1 | 94.5 | 0.55 |
| | 984.5 | 1150 | 61.6 | 58.3 | 94.7 | 0.54 |

Constant Test Conditions: 1.0 LHSV, 2.0 S/O, 100 cc catalyst.
Feed: Ethylbenzene, 99+% purity.

TABLE III

| Catalyst | OPR. HRS | TEMP °F. | % Conv | % Yield | % Select | B/T |
|---|---|---|---|---|---|---|
| Comp. | 26.5 | 1150 | 71.6 | 62.4 | 87.2 | 0.42 |
| Catalyst | 73.0 | 1150 | 75.0 | 63.9 | 85.2 | 0.36 |
| I | 96.0 | 1150 | 76.1 | 64.6 | 84.9 | 0.35 |
| | 119.5 | 1150 | 76.7 | 65.0 | 84.9 | 0.36 |
| | 143.0 | 1150 | 76.3 | 64.9 | 85.1 | 0.34 |
| | 167.5 | 1150 | 76.3 | 64.7 | 84.8 | 0.35 |
| | 191.0 | 1150 | 74.9 | 63.6 | 85.0 | 0.35 |
| | 215.5 | 1150 | 75.5 | 64.1 | 85.0 | 0.35 |
| | 239.5 | 1150 | 74.9 | 63.9 | 85.3 | 0.36 |
| | 263.0 | 1150 | 76.2 | 64.5 | 84.7 | 0.35 |
| | 288.0 | 1150 | 76.5 | 64.9 | 84.8 | 0.35 |
| | 312.0 | 1150 | 76.8 | 65.0 | 84.7 | 0.36 |
| | 336.0 | 1150 | 77.4 | 65.7 | 84.9 | 0.36 |
| | 362.0 | 1150 | 77.3 | 66.0 | 85.4 | 0.36 |
| | 363.0 | Test temporarily interrupted to remove blockage in vaporizer. | | | | |
| | 384.5 | 1150 | 72.4 | 62.9 | 86.7 | 0.36 |
| | 411.0 | 1150 | 73.0 | 63.0 | 86.3 | 0.35 |
| | 433.5 | 1150 | 73.5 | 63.5 | 86.4 | 0.36 |
| | 456.5 | 1150 | 73.2 | 63.3 | 86.5 | 0.37 |
| | 480.5 | 1150 | 73.2 | 63.2 | 86.3 | 0.39 |
| | 503.5 | 1150 | 72.3 | 62.6 | 86.6 | 0.40 |
| | 525.5 | 1150 | 73.4 | 63.6 | 86.7 | 0.41 |
| | 557.0 | 1150 | 76.1 | 66.3 | 87.2 | 0.42 |
| | 576.0 | 1150 | 76.5 | 66.5 | 86.9 | 0.43 |
| | 599.0 | 1150 | 75.5 | 66.0 | 87.4 | 0.43 |
| | 623.0 | 1150 | 76.2 | 66.3 | 87.1 | 0.44 |
| | 647.5 | 1150 | 75.8 | 66.3 | 87.4 | 0.44 |
| | 671.5 | 1150 | 75.4 | 66.1 | 87.6 | 0.45 |
| | 695.5 | 1150 | 73.0 | 64.3 | 88.2 | 0.47 |
| | 718.5 | 1150 | 73.6 | 64.9 | 88.2 | 0.48 |
| | 744.0 | 1150 | 72.6 | 64.5 | 88.8 | 0.49 |
| | 748.5 | Test prematurely ended due to blocked vaporizer. | | | | |

Constant Test Conditions: 1.0 LHSV, 2.0 S/O, 4 psig, 100 cc catalyst.
Feed: Ethylbenzene, 99+% purity.

Further testing was conducted to demonstrate the improved stability, at relatively low steam to oil, of the invention catalyst as compared to a commercially available "high selectivity" catalyst, comparison catalyst IV, having a nominal composition of about: 70.0% $Fe_2O_3$; 23% $K_2CO_3$, 5% $CeO_2$, 1% $V_2O_5$, 1% $Cr_2O_3$. Increased reaction pressure, reduced steam to oil, and reduced temperature are conditions generally accepted to reduce stability of iron oxide type dehydrogenation catalysts. Comparison catalyst IV and the catalyst of the invention were activated over approximately 130 hours at 1150° F. The catalysts were then evaluated at constant conditions of 1.0 LHSV, 1.5 steam to oil by weight, 4 psig reaction pressure and 1050° F.

TABLE IV

| Catalyst | OPR. HRS | TEMP °F. | % Conv | % Yield | % Select | B/T |
|---|---|---|---|---|---|---|
| Invention | 24.5 | 1150 | 57.6 | 54.2 | 94.0 | 0.83 |
| Catalyst | 48.0 | 1150 | 63.2 | 59.1 | 93.5 | 0.76 |
| Example I | 71.5 | 1150 | 61.4 | 57.8 | 94.2 | 0.71 |
| | 91.5 | 1150 | 61.1 | 57.6 | 94.3 | 0.72 |
| | 118.5 | 1150 | 61.4 | 57.8 | 94.2 | 0.74 |
| | 149.5 | 1050 | 25.4 | 25.3 | 99.7 | 0.38 |
| | 167.5 | 1050 | 25.1 | 25.1 | 99.7 | 0.37 |
| | 191.5 | 1050 | 25.0 | 24.9 | 99.5 | 0.35 |
| | 215.0 | 1050 | 25.2 | 25.1 | 99.6 | 0.41 |
| | 239.5 | 1050 | 25.6 | 25.4 | 99.5 | 0.40 |
| Comp. | 22.5 | 1150 | 64.1 | 59.9 | 93.5 | 0.68 |
| Catalyst | 43.5 | 1150 | 62.0 | 58.1 | 93.8 | 0.71 |
| IV | 67.5 | 1150 | 61.5 | 57.5 | 93.5 | 0.74 |
| | 91.5 | 1150 | 60.2 | 56.5 | 93.9 | 0.70 |
| | 115.5 | 1150 | 59.1 | 55.5 | 93.8 | 0.70 |
| | 138.5 | 1150 | 59.7 | 56.0 | 93.8 | 0.69 |
| | 168.5 | 1050 | 28.4 | 28.0 | 99.4 | 0.25 |
| | 162.5 | 1050 | 25.9 | 25.7 | 99.4 | 0.25 |
| | 216.0 | 1050 | 26.1 | 26.0 | 99.5 | 0.25 |
| | 235.0 | 1050 | 24.7 | 24.5 | 99.4 | 0.25 |

TABLE IV-continued

| Catalyst | OPR. HRS | TEMP °F. | % Conv | % Yield | % Select | B/T |
|---|---|---|---|---|---|---|
| | 259.5 | 1050 | 25.7 | 25.5 | 99.3 | 0.24 |
| | 282.5 | 1050 | 23.8 | 23.7 | 99.5 | 0.25 |
| | 307.5 | 1050 | 23.5 | 23.4 | 99.6 | 0.23 |
| | 330.5 | 1050 | 23.5 | 23.4 | 99.6 | 0.28 |
| | 355.0 | 1050 | 23.1 | 23.0 | 99.7 | 0.29 |
| | 379.5 | 1050 | 22.0 | 22.5 | 99.8 | 0.26 |

Constant Test Conditions: 1.0 LHSV, 2.0 S/O, 4 psig, 100 cc catalyst.
Feed: Ethylbenzene, 99+% purity.

Figure 4:
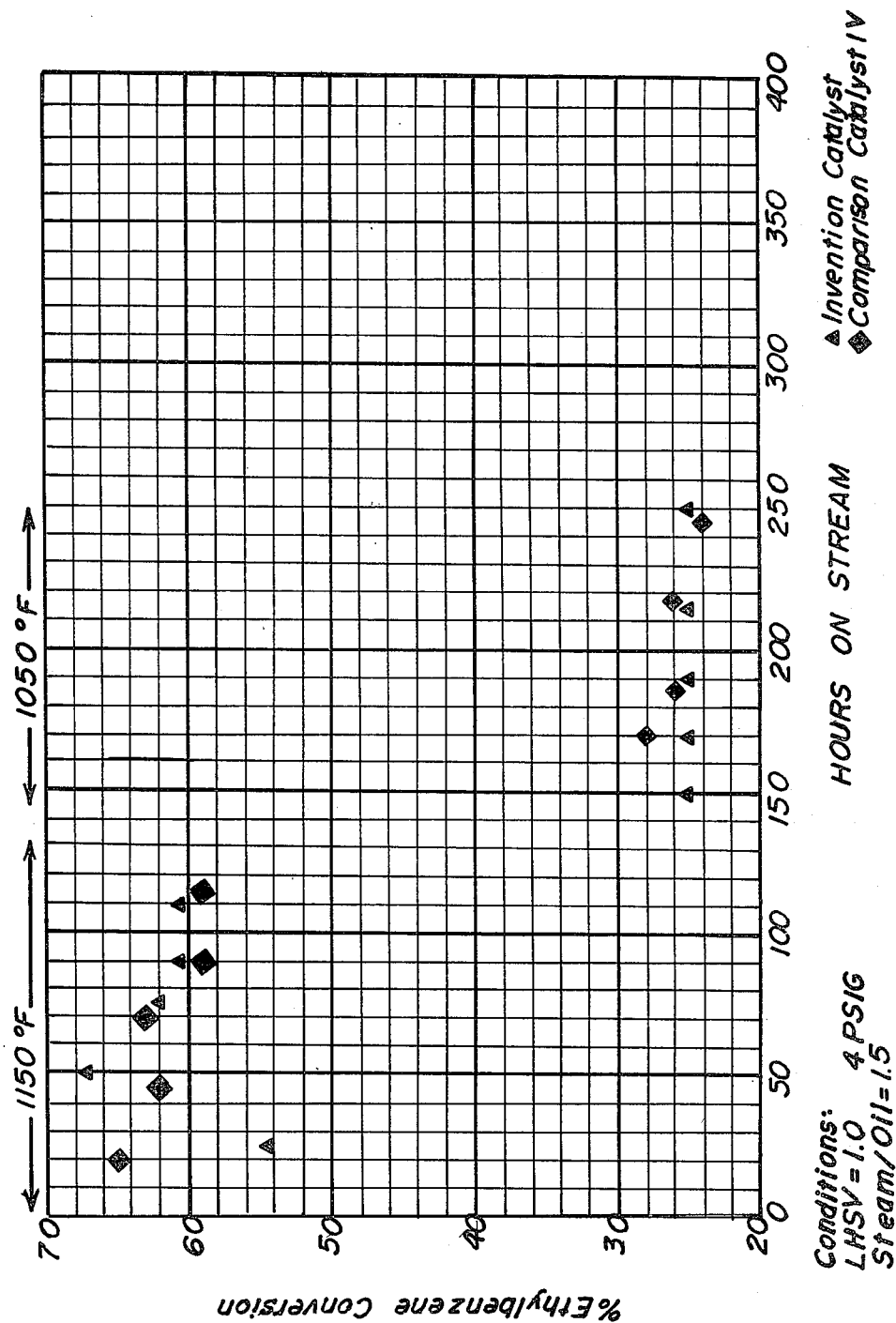
FIG. 4 is a graphic representation comparing the performance of the invention catalyst and comparison catalyst IV.

The test results are presented in table IV and shown graphically in FIG. 4 where a plot of conversion versus time on stream serves to demonstrate the relatively greater stability of the invention catalyst versus comparison catalyst IV. Comparison catalyst IV exhibits a slight decrease inactivity over the activation period at 1150° F. while the catalyst of the invention does not. The same results are observed at 1050° F. with the decline in performance of comparison catalyst IV becoming even more apparent.

It is to be understood that various other compositions also within the scope of the present invention will occur to those skilled in the art upon reading the disclosure set forth hereinbefore.

The invention claimed is:

1. A dehydrogenation catalyst including 15 to 30% by weight of a compound selected from the group consisting of the oxide and carbonate of an alkali metal 2% to 8% by weight of cerium oxide, 1.5 to 6.0% by weight of molybdenum oxide, 1 to 8% by weight of a compound selected from the group consisting of the oxide and carbonate of calcium and the balance iron oxide for the dehydrogenation of organic alkyl materials to correspondingly less saturated materials.

2. The catalyst of claim 1 including 2 to 8.0% by weight of a chromium oxide.

3. The catalyst of claim 1 wherein the alkali metal is potassium carbonate.

4. The catalyst of claim 1 wherein the calcium compound is calcium carbonate.

5. The catalyst of claim 1 wherein the calcium compound is calcium oxide.

* * * * *